United States Patent
Copland et al.

(10) Patent No.: US 11,311,187 B2
(45) Date of Patent: Apr. 26, 2022

(54) METHODS AND SYSTEMS FOR CORNEAL TOPOGRAPHY WITH IN-FOCUS SCLERAL IMAGING

(71) Applicant: AMO Development, LLC, Santa Ana, CA (US)

(72) Inventors: Richard J. Copland, Albuquerque, NM (US); Daniel R. Neal, Tijeras, NM (US)

(73) Assignee: AMO Development, LLC, Santa Ana, CA (US)

(*) Notice: Subject to any disclaimer, the term of this patent is extended or adjusted under 35 U.S.C. 154(b) by 221 days.

(21) Appl. No.: 16/375,718

(22) Filed: Apr. 4, 2019

(65) Prior Publication Data
US 2019/0307326 A1 Oct. 10, 2019

Related U.S. Application Data

(60) Provisional application No. 62/654,124, filed on Apr. 6, 2018.

(51) Int. Cl.
*A61B 3/00* (2006.01)
*A61B 3/107* (2006.01)
(Continued)

(52) U.S. Cl.
CPC .......... *A61B 3/0008* (2013.01); *A61B 3/0025* (2013.01); *A61B 3/102* (2013.01);
(Continued)

(58) Field of Classification Search
CPC ......... A61B 3/152; A61B 3/0058; A61B 3/13; A61B 1/0661; A61B 3/158; A61B 3/107;
(Continued)

(56) References Cited

U.S. PATENT DOCUMENTS

| | | |
|---|---|---|
| 5,329,322 A | 7/1994 | Yancey |
| 5,777,719 A | 7/1998 | Williams et al. |

(Continued)

FOREIGN PATENT DOCUMENTS

| | | |
|---|---|---|
| CN | 101721196 A | 6/2010 |
| WO | 03098312 A1 | 11/2003 |
| WO | 2008011003 A2 | 1/2008 |

OTHER PUBLICATIONS

Mejia-Barbosa Y., et al., "Object Surface For Applying A Modified Hartmann Test To Measure Corneal Topography," Applied Optics, Nov. 1, 2001, vol. 40 (31), pp. 5778-5786.

(Continued)

*Primary Examiner* — Mustak Choudhury
(74) *Attorney, Agent, or Firm* — Johnson & Johnson Surgical Vision, Inc.

(57) ABSTRACT

A system includes: a group of first light sources arranged around a central axis, the group being separated from the axis by a radial distance defining an aperture in the group; a plurality of second light sources; a detector array; and an optical system adapted to provide light from the second light sources through the aperture to a cornea of an eye, and to provide images of the first light sources and images of the second light sources from the cornea, through the aperture, to the detector array. The optical system includes a field flattener such that a shape of a surface of best focus on the detector array curves away from detector array in generally a same direction as the eye and a sclera of the eye.

17 Claims, 10 Drawing Sheets

(51) Int. Cl.
*A61B 3/10* (2006.01)
*A61B 3/117* (2006.01)
*A61B 3/14* (2006.01)

(52) U.S. Cl.
CPC .............. *A61B 3/107* (2013.01); *A61B 3/117* (2013.01); *A61B 3/14* (2013.01)

(58) Field of Classification Search
CPC ..... A61B 3/0008; A61B 3/0025; A61B 3/102; A61B 3/117; A61B 3/14; F21Y 2115/10; F21Y 2115/30; F21Y 2101/00; F21K 9/64
See application file for complete search history.

(56) References Cited

U.S. PATENT DOCUMENTS

| | | | |
|---|---|---|---|
| 6,024,449 A * | 2/2000 | Smith | A61B 3/107 351/212 |
| 6,550,917 B1 | 4/2003 | Neal et al. | |
| 6,741,359 B2 | 5/2004 | Wei et al. | |
| 7,723,657 B2 * | 5/2010 | Altendorf | G01B 11/0608 250/201.2 |
| 7,976,163 B2 | 7/2011 | Campbell et al. | |
| 7,980,699 B2 | 7/2011 | Neal et al. | |
| 9,119,563 B2 | 9/2015 | Buckland et al. | |
| 2007/0195268 A1 | 8/2007 | Sarver et al. | |
| 2008/0018856 A1 | 1/2008 | Sarver et al. | |
| 2014/0276670 A1 | 9/2014 | Schlueter et al. | |
| 2014/0354950 A1 | 12/2014 | Buckland et al. | |
| 2015/0085294 A1 | 3/2015 | Wang et al. | |
| 2016/0095752 A1 * | 4/2016 | Srinivasan | A61F 9/00827 606/6 |
| 2017/0202455 A1 | 7/2017 | Farrer et al. | |

OTHER PUBLICATIONS

International Search Report and Written Opinion for Application No. PCT/IB2019/052759, dated Jul. 25, 2019, 13 pages.

* cited by examiner

METHODS AND SYSTEMS FOR CORNEAL TOPOGRAPHY WITH IN-FOCUS SCLERAL IMAGING

CROSS REFERENCE TO RELATED APPLICATIONS

This application claims the benefit under 35 U.S.C. § 119(e) of U.S. Provisional Patent Application No. 62/654,124, filed Apr. 6, 2018, which is incorporated herein by reference in its entirety.

TECHNICAL FIELD

Embodiments of this invention pertain to optical measurement systems and methods, and more particularly, to optical measurement systems and methods which employ corneal topography.

BACKGROUND

Corneal topography, also sometimes referred to as photokeratoscopy and videokeratoscopy, is a technique that is used to map the curved surface of the cornea. Corneal topography data can help measure the quality of vision as well as assist in eye surgery and in the fitting of contact lenses. Various types of corneal topographers and methods are known, including Placido ring topographers, Scheimpflug imagers, and more recently, point source color LED topographers (CLT).

Corneal topography data for an eye may be obtained by a corneal topographer in a diagnostic or examination setting, and then it is desired to use this corneal topography data during a subsequent eye treatment procedure such as laser-assisted in situ keratomileusis ("LASIK") or implantation of an intra-ocular lens (IOL). However, to use the corneal topography data, obtained in an eye examination, for a subsequent eye treatment procedure, it is necessary to register the data to the locations of some features, which can be recognized during the eye treatment procedure. This registration is particularly important for implantation of a toric IOL designed to correct astigmatism. In this case, the alignment of the IOL to the corneal topography data must be accurately achieved to correct for the desired astigmatism.

One solution is to make ink marks on the eye that can be seen during the corneal topography examination, and then use similar ink marks during surgery. However, there are accuracy limitations to this approach and the creation of the ink marks can add time and discomfort to the procedures.

A second solution is that features on the iris of the eye are used for registration. But, accuracy of iris registration can be problematic, because during cataract surgery, IOL placement, and other procedures, pharmaceuticals are placed in the eye, which cause the pupil to dilate. Hence, the feature set that is available for registration to the corneal topography data is very narrow and not reliable.

It would therefore be desirable to provide a corneal topographer and a method of performing corneal topography, which can register the corneal topography data to the locations of features, which can be recognized during a subsequent eye treatment procedure.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION

Exemplary embodiments of optical measurement systems and methods for measuring aberrations of an eye to illustrate various aspects and advantages of these devices and methods are described below. But, since principles involved in these devices and methods can be employed in a variety of other contexts, the novel devices and method disclosed and claimed here should not be construed as being limited to the examples of embodiments described below.

As used herein the term "light source" means a source of electromagnetic radiation, particularly a source in or near the visible band of the electromagnetic spectrum, for example, in the infrared, near infrared, or ultraviolet bands of the electromagnetic radiation. As used herein, the term "light" may be extended to mean electromagnetic radiation in or near the visible band of the electromagnetic spectrum, for example, in the infrared, near infrared, or ultraviolet bands of the electromagnetic radiation.

Figure 1:
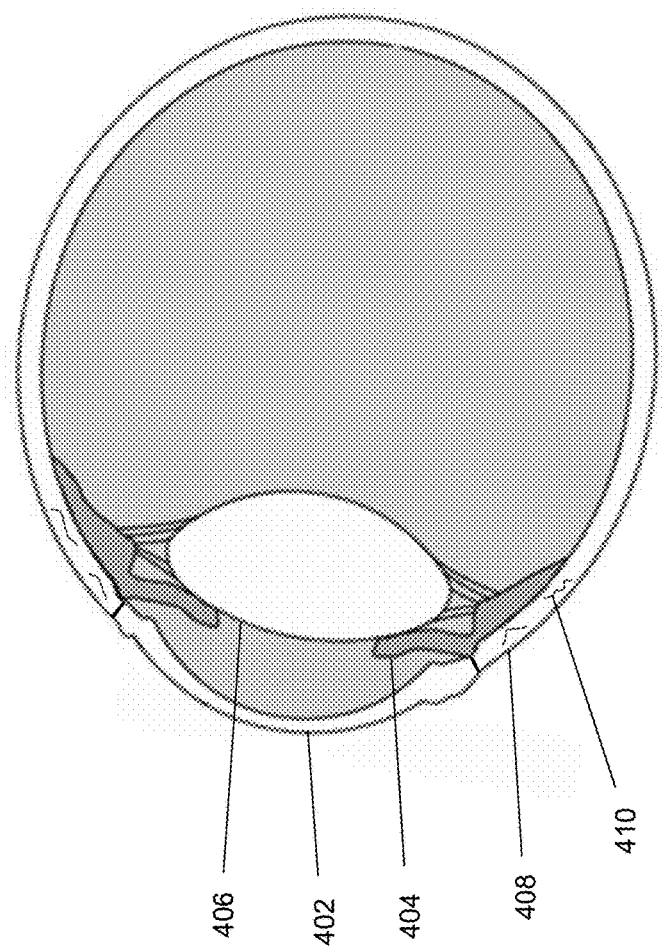
FIG. 1 is a schematic drawing of a portion of a human eye.

FIG. 1 is a schematic drawing of a portion of a human eye 101 which can be used in the explanations below. Eye 101 includes, in relevant part, a cornea 402, an iris 404, a lens 406 and a sclera 408. Sclera 408 includes sclera blood vessels 410.

Figure 2:
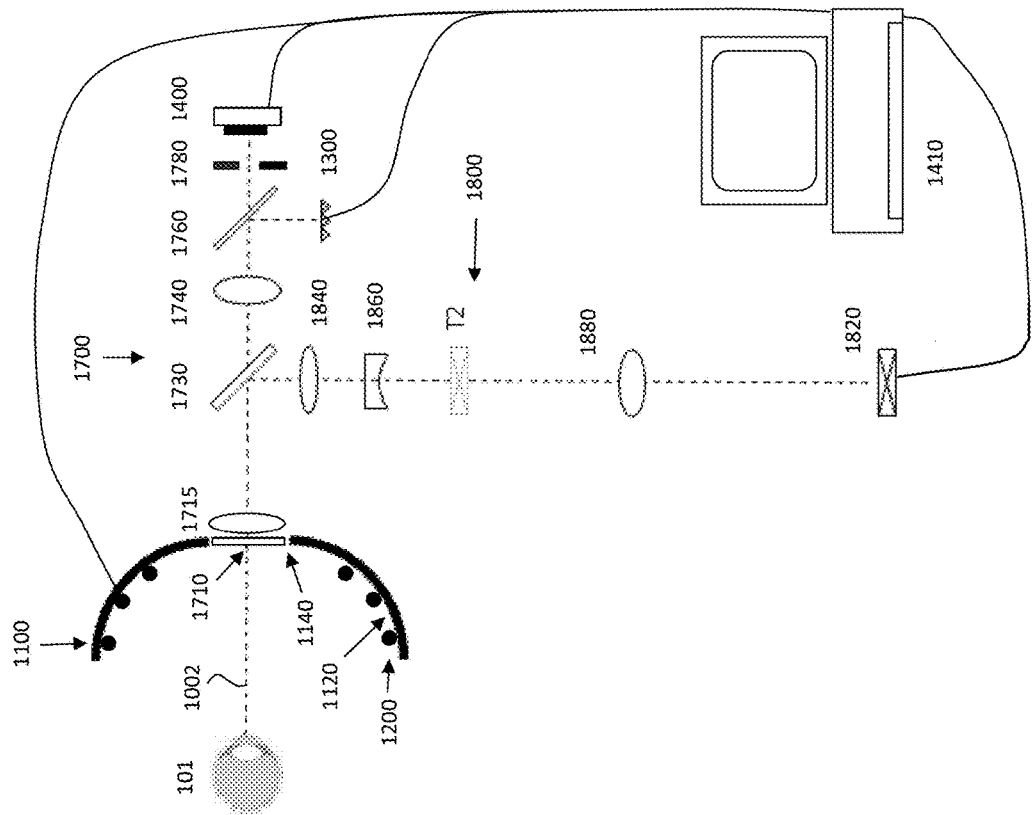
FIG. 2 illustrates an example embodiment of a corneal topographer.

FIG. 2 illustrates an example embodiment of a corneal topographer 2000.

Corneal topographer 2000 comprises a structure 1100 having a principal surface 1120 with an opening or aperture 1140 therein; a plurality of first (or peripheral) light sources 1200 provided on the principal surface 1120 of the structure 1100; a plurality of second, or central, light sources 1300 (also sometimes referred to as "Helmholtz light sources"); a camera 1400 including a detector array; a processor 1410; and an optical system 1700 disposed along a central axis 1002 passing through the opening or aperture 1140 of the structure 1100. Optical system 1700 comprises a quarter-wave plate 1710, a first optical element (e.g., a positive lens) 1715, a beamsplitter 1730, a second optical element (e.g., a positive lens) 1740, a second beamsplitter 1760, and a structure including an aperture 1780. It will be appreciated by those of skill in the art that the lenses 1715, 1730, or any of the other lenses discussed herein, may be replaced or supplemented by another type of converging or diverging optical element, such as a diffractive optical element. Beneficially, system 1000 further comprises a fixation target system 1800, comprising light source 1820 and lenses 1840, 1860, and 1880. In an alternative embodiment, second optical element (e.g., a positive lens) 1740 may be repositioned so it is disposed between aperture 1780 and camera 1400.

Further details regarding the construction and operation of corneal topographer 2000 may be found in U.S. Pat. No. 7,976,163, "SYSTEM AND METHOD FOR MEASURING CORNEAL TOPOGRAPHY," to Campbell et al., which is hereby incorporated herein in its entirety as if fully set forth herein. Accordingly, a further discussion of the details of the construction and operation of corneal topographer 2000 will be omitted from the discussion below.

As described above, to use corneal topography data which is obtained in a diagnostic or examination setting (for example with corneal topographer 2000), during a subsequent eye treatment procedure, it is necessary to register the corneal topography data to the locations of some features which can be recognized during the eye treatment procedure.

One set of features which may be employed for registration to corneal topography data are sclera blood vessels 410 of sclera 408.

Figure 3:
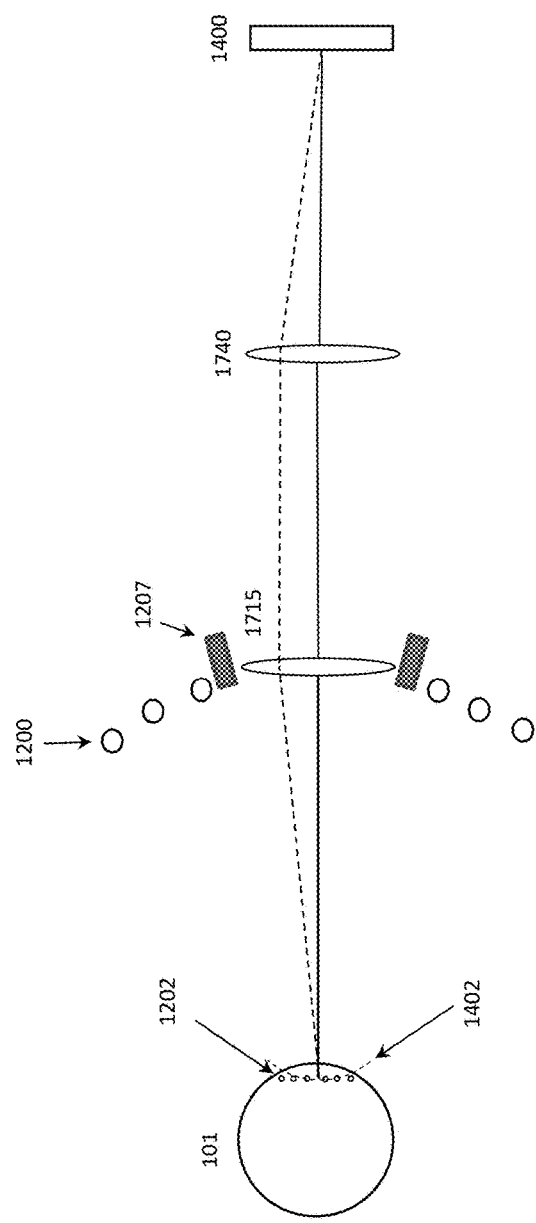
FIG. 3 illustrates an example of an arrangement of a corneal topographer creating and capturing a virtual image from eye.

FIG. 3 illustrates an example of an arrangement 3000 of a corneal topographer creating and capturing a virtual image from eye 101. FIG. 3 is provided to illustrate certain points regarding the optical paths and characteristics of arrangement 3000, and so many elements of the corneal topographer have been omitted for simplification. In some embodiments, the corneal topographer of arrangement 3000 may be corneal topographer 2000.

As shown in FIG. 3, light sources 1200 create a virtual image 1202 on cornea 1402 of eye 101 which is viewed by camera 1400 through the telecentric arrangement of lenses 1715 and 1740. Corneal topography data for eye 101 is produced from the light produced on camera 1400 by virtual image 1202. Illumination for the sclera and iris features of the eye is provided by light sources 1207. Camera 1400 may also view sclera blood vessels 410 in sclera 408 at the same time as virtual image 1202 from which the corneal topography data is produced.

However, arrangement 3000 suffers from some deficiencies.

In particular, eye 101 and sclera 410 have curved surfaces, which "curve away" from the flat surface of camera 1400. As a result, sclera blood vessels 410 are located a few millimeters further from the corneal topographer and camera 1400 than virtual image 1202 of the array of light sources 1200. Meanwhile, it is natural situation that imaging systems with simple optics and a flat sensor (e.g., camera 1400) will exhibit positive field curvature. As a result, the shape of a surface 1402 of best focus on the sensor surface or detector array of camera 1400, illustrated with a dashed line in FIG. 3, "curves in toward" camera 1400—which is the opposite direction as eye 101 and sclera 410 which curve away from camera 1400.

Consequently, sclera blood vessels 410 are out of focus at the sensor surface or detector array of camera 1400 and do not form a feature set to which the corneal topographer data can be registered.

One technique which may be employed to address this problem is to use a camera and lens combination with a very high f-number (e.g., f/14) to image features of sclera 408, such as blood vessels 410, during the corneal topographer measurements. For a simple system, the f-number is defined as the ratio of the lens focal length divided by the lens diameter. For example, if a lens' focal length is 20 mm and its entrance pupil diameter is 10 mm, the f-number is 2 and this is written as "f/2." A high f-number is accomplished by having a small aperture in the beam path. The effect is to increase the depth of field of the imaging system.

However, a disadvantage to this technique is that the high f-number requires that light sources 1200 be very bright to obtain good corneal topography data. Meanwhile, it becomes difficult to make the brightness of light sources 1200 high enough in a cost-effective manner. Also, illumination from the light sources 1207 causes the blood vessels show up with high contrast if the wavelengths are in the green range, but with low contrast if the wavelengths are in the red or infrared range, because the white of the sclera reflects both red and infrared wavelengths equally as well as the blood vessels. So red or infrared lighting is not practical for imaging scleral blood vessels. A high f-number optical system would require the green lights to be so bright that patient discomfort would result since the eye is particularly sensitive to green light. Systems and methods described below enable the use of optical arrangements with low f-numbers that efficiently collect light from the eye and allow for patient comfort, Toward this end, the present inventors have devised a solution which involves modifying the optical system which delivers light from eye 101 to camera 1400 to include a field flattener so that the shape of the surface of best focus at the sensor surface or detector array of camera 1400 "curves away" from camera 1400 in the same manner as the surfaces of eye 101 and sclera 408. An image of the eye, blood vessels 410 of sclera 408, is captured at the same time as the corneal topography data is obtained by capturing virtual image 1202 of corneal topographer light sources 1200. Illumination for the sclera and iris features of the eye is provided by light sources 1207. By this arrangement, blood vessels 410 of sclera 408 may appear in focus at the sensor surface or detector array of camera 1400 and may therefore be used as registration markers or fiducials for registration with the corneal topography data which is obtained at the same time as the image of the eye.

Figure 4A:
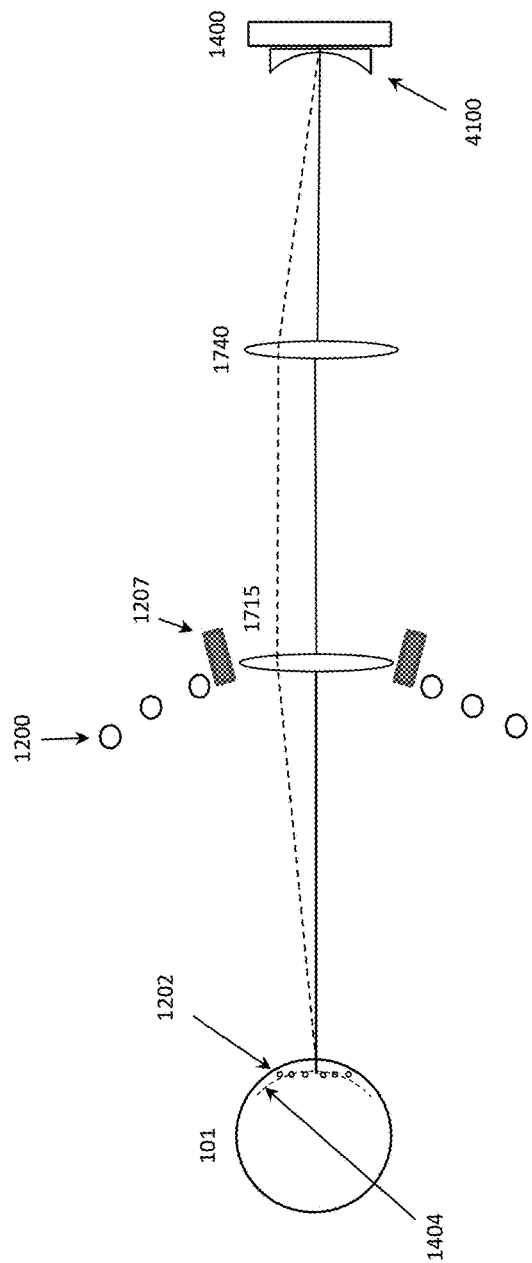
FIG. 4A illustrates an example of an arrangement of a corneal topographer having improved ability to register the corneal topography data to the locations of sclera blood vessels in the eye.

FIG. 4A illustrates an example of an arrangement 4000 of a corneal topographer having improved ability to register the corneal topography data to the locations of scleral blood vessels 410 in eye 101. To simply the drawing, various elements of corneal topographer 2000, such as the processor and fixation target system, are not shown in FIG. 4A (or in FIG. 4B below).

As before, light sources 1200 create a virtual image 1202 on cornea 402 of eye 101. Camera 1400 may also view sclera blood vessels 410 in sclera 408 at the same time as virtual image 1202 from which the corneal topography data is produced.

In contrast to arrangement 3000, however, arrangement 400 includes a field flattener to offset the positive field curvature illustrated in arrangement 3000. In arrangement 4000, the field flattener comprises a strong negative lens 4100 in the optical system between eye 101 and camera 1400. Due to the presence of the field flattener (e.g., negative lens 4100), in arrangement 4000, the shape of a surface 1404 of best focus on the sensor surface or detector array of camera 1400, illustrated with a dashed line in FIG. 4A, "curves away" from camera 1400—in generally the same direction as eye 101 and sclera 410. Camera 1400 views virtual image 1202 and sclera blood vessels 410 through the optical system, comprising positive lenses 1715 and 1740 and negative lens 4100 disposed immediately in front of camera 1400. As a result, sclera blood vessels 410 may be in focus or nearly in focus at the sensor surface or detector array of camera 1400. Corneal topography data for eye 101 is produced from the light produced on camera 1400 by virtual image 1202, and blood vessels 410 are viewed by camera 1400 and identified by an associated processor (not shown in FIG. 4A) to be used as fiducials or registration markers for the corneal topography data for eye 101.

A modified version of corneal topographer 2000 may be employed in arrangement 4000, wherein negative lens 4100 may be inserted in the optical path between aperture 1780 and camera 1400.

Figure 4B:
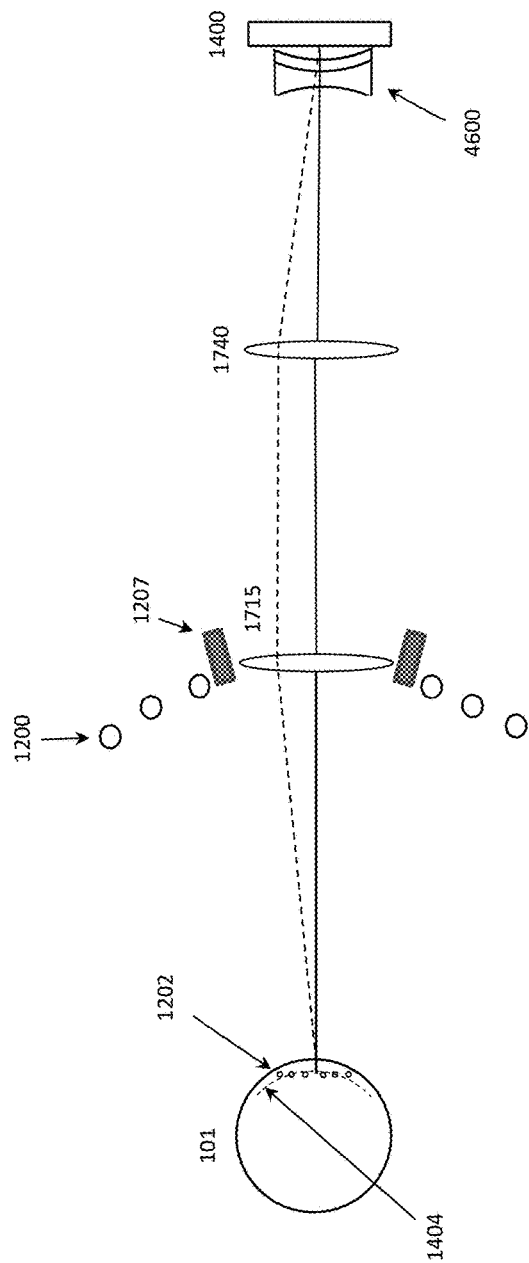
FIG. 4B illustrates another example of an arrangement of a corneal topographer having improved ability to register the corneal topography data to the locations of sclera blood vessels in the eye.

Although arrangement 4000 employs negative lens 4100 as a field flattener, other devices may be employed as field flatteners in other arrangements. For example, negative lenses tend to have noticeable astigmatism near the edge of the image. Accordingly, an alternative embodiment may use a two element "negative achromatic lens" that has much less off-axis astigmatism FIG. 4B illustrates another example of an arrangement 4500 of a corneal topographer having improved ability to register the corneal topography data to the locations of scleral blood vessels 410 in eye 101. Arrangement 4500 is identical in configuration and operation to arrangement 4000, except that negative achromatic lens 4600 is substituted for negative lens 4100 as a field flattener. Accordingly, a further description of arrangement 4500 is omitted.

Although FIGS. 4A and 4B illustrate example embodiments, which include a corneal topographer, which uses a group of individual light sources 1200 as light spot generators to produce individual light spots on the cornea, in other embodiments, other corneal topographers for generating other light patterns on the cornea may be employed instead.

Figure 5:
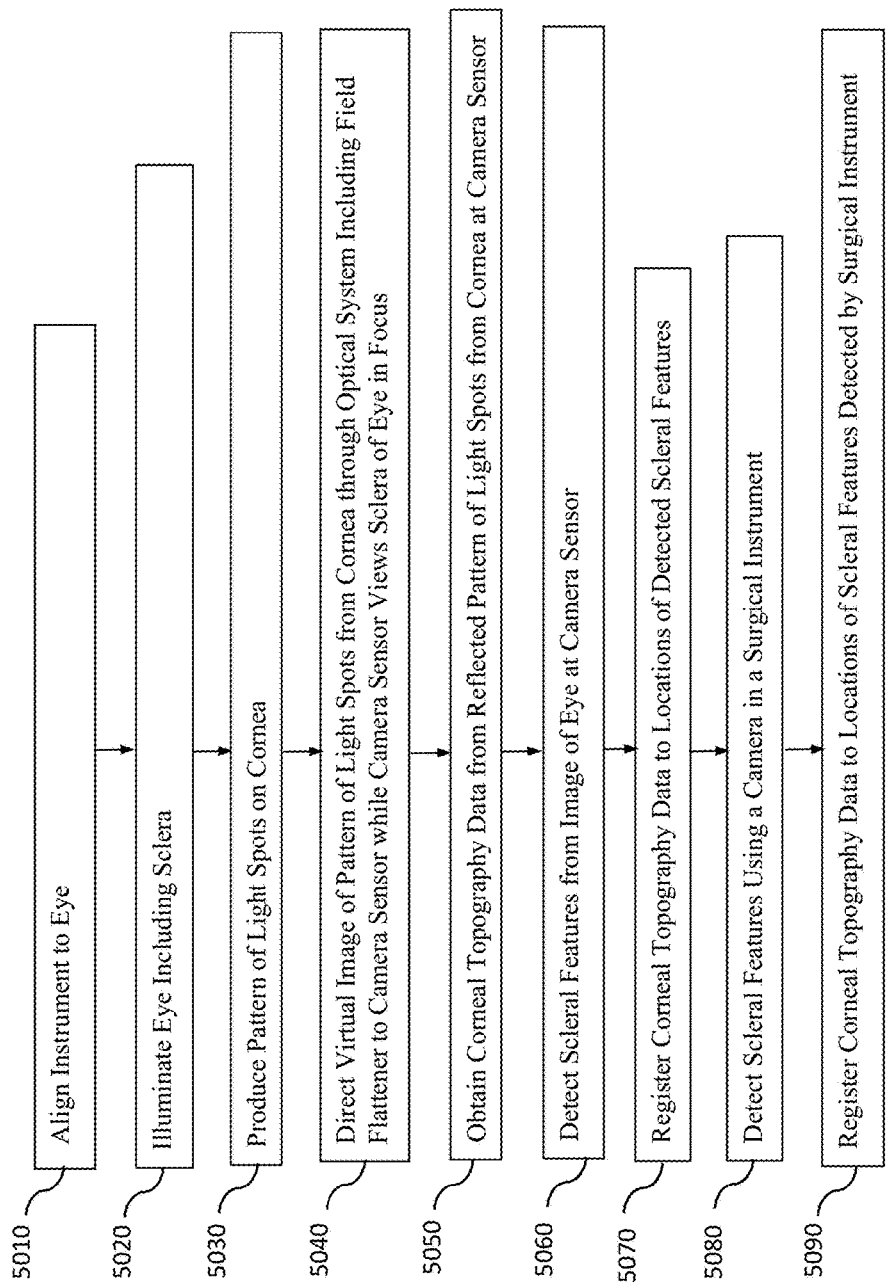
FIG. 5 is a flowchart of an example embodiment of a method of measuring a corneal topography of an eye.

FIG. 5 is a flowchart of an example embodiment of a method 5000 of measuring one or more characteristics of an eye with a corneal topographer such as corneal topographer 2000 using an arrangement such as arrangement 4000 or arrangement 4500.

An operation 5010 includes aligning the measurement instrument, including the corneal topographer, to the eye under examination.

An operation 5020 includes illuminating the sclera of the eye under examination.

An operation 5030 includes producing a pattern of light spots on the cornea of the eye under examination.

An operation 5040 includes directing a virtual image of the pattern of light spots from the cornea of the eye under examination, through an optical system which includes a field flattener, to a camera sensor while the camera views the sclera of the eye under examination, in focus.

An operation 5050 includes obtaining Corneal Topography data from the reflected pattern of light spots from the cornea which appears at the camera sensor.

An operation 5060 includes detecting sclera features (e.g., blood vessels) from the image of the eye at the camera sensor.

An operation 5070 includes registering the corneal topography data to the locations of the detected sclera features.

After operations 5010 through 5070, the corneal topography data, which is obtained through those operations may be employed by a surgical instrument in an eye surgery, such as LASIK, or cataract surgery involving an implantation of an IOL.

In that case, an operation 5080 includes using a camera in a surgical instrument to detect the same sclera features which were previously detected in operation 5060 and to whose locations the corneal topography data was registered in operation 5070.

An operation 5090 includes the surgical instrument registering the corneal topography data to the locations of the sclera features which are detected by the surgical instrument, using the registration of the corneal topography data which was performed earlier in operation 5070.

The principles of OCT interferometers 1000, 3000 and 4000 as described above, may be applied to an optical measurement instrument which includes additional functionality, such as the ability to measure corneal topography and/or to make wavefront aberrometry measurements for they eye. Embodiments of such an optical measurement instrument, and methods of operation thereof, will now be described.

Figure 6C:
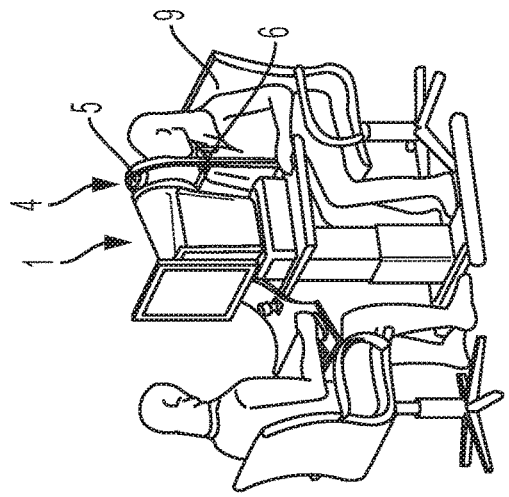
FIG. 6C illustrates a side perspective view showing an optical measurement system according to many embodiments.
Figure 6A:
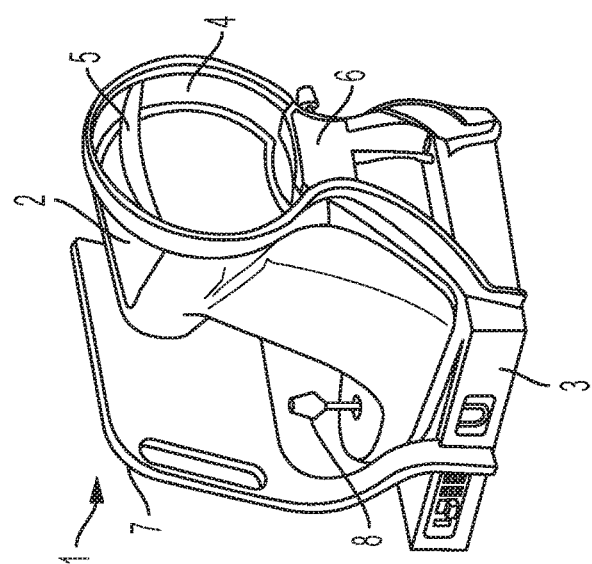
FIG. 6A illustrates a front perspective view showing an optical measurement system according to many embodiments.
Figure 6B:
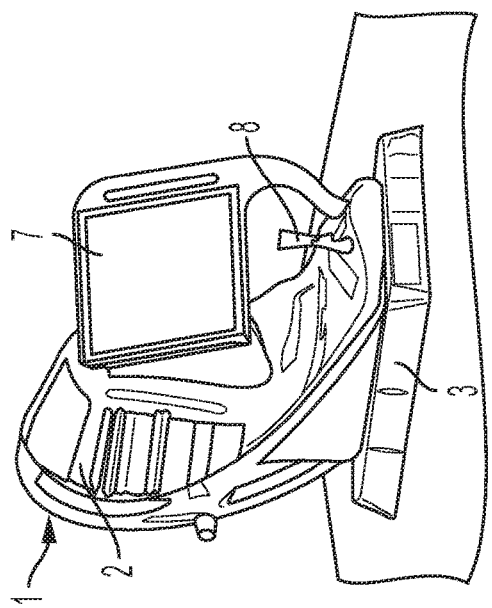
FIG. 6B illustrates a rear perspective view showing an optical measurement system according to many embodiments.

As shown in FIGS. 6A-6C, an optical measurement system 1, according to many embodiments, is operable to provide for a plurality of measurements of the human eye, including wavefront aberrometry measurements, corneal topography measurements, and optical coherence tomography measurements to measure characteristics of the cornea, the lens capsule, the lens and the retina. Optical measurement system 1 includes a main unit 2 which comprises a base 3 and includes many primary subsystems of many embodiments of optical measurement system 1. For example, externally visible subsystems include a touch-screen display control panel 7, a patient interface 4 and a joystick 8.

Patient interface 4 may include one or more structures configured to hold a patient's head in a stable, immobile and comfortable position during the diagnostic measurements while also maintaining the eye of the patient in a suitable alignment with the diagnostic system. In a particularly preferred embodiment, the eye of the patient remains in substantially the same position relative to the diagnostic system for all diagnostic and imaging measurements performed by optical measurement system 1.

In one embodiment patient interface 4 includes a chin support 6 and/or a forehead rest 5 configured to hold the head of the patient in a single, uniform position suitably aligned with respect to optical measurement system 1 throughout the diagnostic measurement. As shown in FIG. 6C, the optical measurement system 1 may be disposed so that the patient may be seated in a patient chair 9. Patient chair 9 can be configured to be adjusted and oriented in three axes (x, y, and z) so that the patent's head can be at a suitable height and lateral position for placement on the patient interface.

In many embodiments, optical measurement system 1 may include external communication connections. For example, optical measurement system 1 can include a network connection (e.g., an RJ45 network connection or WiFi) for connecting optical measurement system 1 to a network. The network connection can be used to enable network printing of diagnostic reports, remote access to view patient diagnostic reports, and remote access to perform system diagnostics. Optical measurement system 1 can include a video output port (e.g., HDMI) that can be used to output video of diagnostic measurements performed by optical measurement system 1. The output video can be displayed on an external monitor for, for example, viewing by physicians or users. The output video can also be recorded for, for example, archival or training purposes. Optical measurement system 1 can include one or more data output ports (e.g., USB) to enable export of patient diagnostic reports to, for example, a data storage device or a computer readable medium, for example a non-volatile computer readable medium, coupled to a laser cataract surgery device for use of the diagnostic measurements in conducting laser cataract surgeries. The diagnostic reports stored on the data storage device or computer readable medium can then be accessed later for any suitable purpose such as, for example, printing from an external computer in the case where the user without access to network based printing or for use during cataract surgery, including laser cataract surgery. Other uses of network data include obtaining service logs, outcomes analysis and algorithm improvement.

Figure 7:
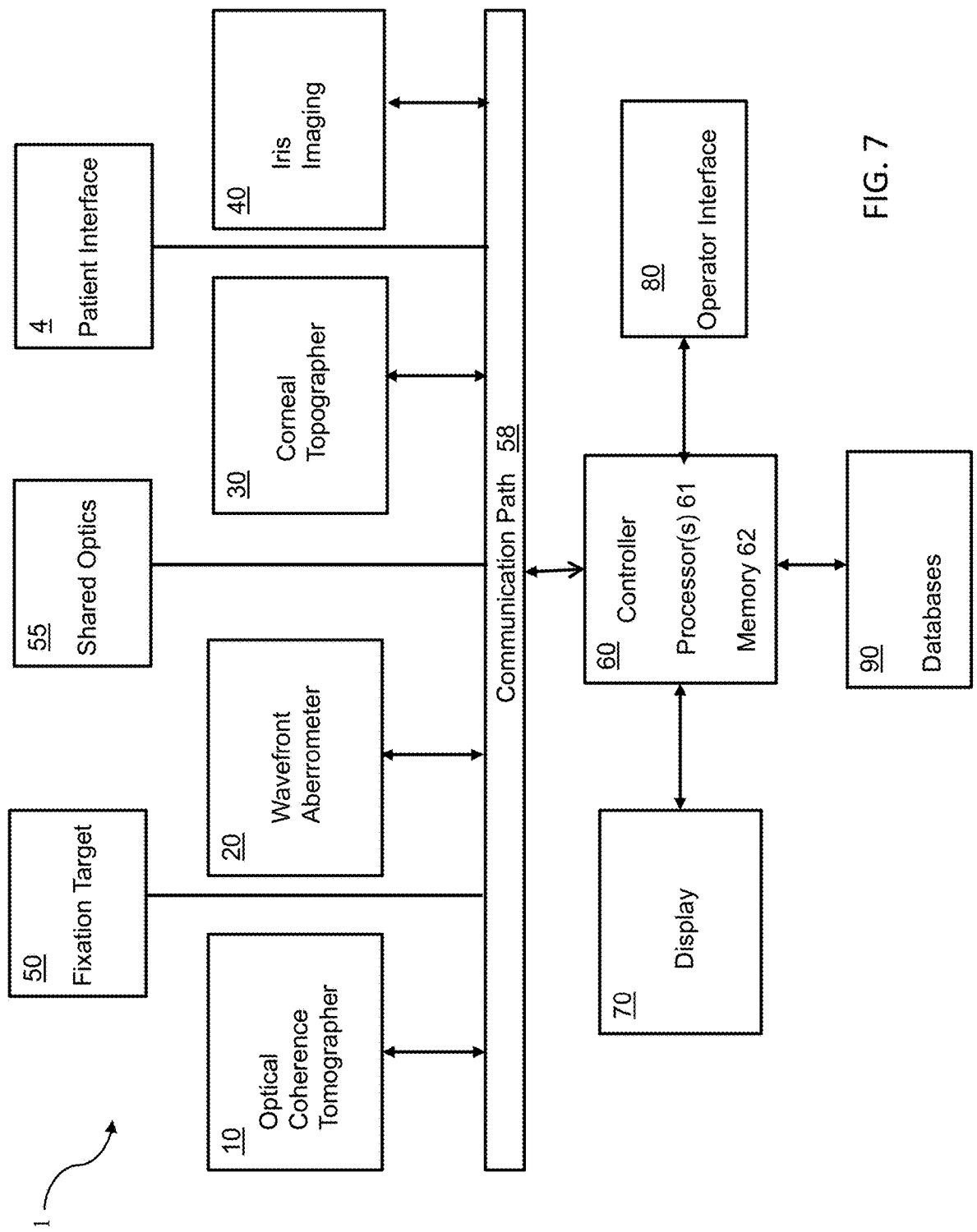
FIG. 7 is a block diagram of a system including an optical measurement instrument, and a position of an eye relative to the system according to one or more embodiments described herein which may be used by the optical measurement.

FIG. 7 is a block diagram of optical measurement system 1 according to one or more embodiments described herein. Optical measurement system 1 includes: an optical coherence tomography (OCT) subsystem 10, a wavefront aberrometer subsystem 20, and a corneal topographer subsystem 30 for measuring one or more characteristics of a subject's eye. Optical measurement system 1 may further include an iris imaging subsystem 40, a fixation target subsystem 50, a controller 60, including one or more processor(s) 61 and memory 62, a display 70 and an operator interface 80. Optical measurement system 1 further includes patient interface 4 for a subject to present his or her eye for measurement by optical measurement system 1.

Optical coherence tomography subsystem 10 is configured to measure the spatial disposition (e.g., three-dimensional coordinates such as X, Y, and Z of points on boundaries) of eye structures in three dimensions. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, the limbus and/or the retina. The spatial disposition of the structures of interest and/or of suitable matching geometric modeling such as surfaces and curves can be generated and/or used by controller 60 for many purposes, including, in some embodiment to program and control a subsequent laser-assisted surgical procedure. The spatial disposition of the structures of interest and/or of suitable matching geometric modeling can also be used to determine a wide variety of parameters. Beneficially, optical coherence tomography subsystem 10 may employ swept source optical coherence tomography (SS-OCT) or spectral domain OCT (SDOCT).

Wavefront aberrometer subsystem 20 is configured to measure ocular aberrations, which may include low and high order aberrations, by measuring the wavefront emerging from the eye by, for example a Shack Hartman sensor.

Corneal topographer subsystem 30 may apply any number of modalities to measure the shape of the cornea including one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Hartmann-Shack measurement of the eye, a Scheimpflug image topography of the eye, a confocal tomography of the eye, a Helmholtz source topographer, or a low coherence reflectometry of the eye. The shape of the cornea should generally be measured while the patient is engaged with patient interface 4. Beneficially, corneal topographer subsystem 30 may comprise corneal topographer 2000 which was discussed and described above, modified to include a field flattener as also discussed and described above.

Fixation target system 50 is configured to control the patient's accommodation and alignment direction, because it is often desired to measure the refraction and wavefront aberrations when an eye under measurement is focused at its far point Images captured by corneal topographer subsystem 10, wavefront aberrometer 20, optical coherence tomographer subsystem 30 or camera 40 may be displayed with a display of operator interface 80 or display 70 of optical measurement system 1, respectively. Operator interface 80 may also be used to modify, distort, or transform any of the displayed images.

Shared optics 55 provide a common propagation path that is disposed between patient interface 4 and each of optical coherence tomography (OCT) subsystem 10, wavefront aberrometer subsystem 20, corneal topographer subsystem 30, and in some embodiments, camera 40, and fixation target 50. In many embodiments, shared optics 55 may comprise many optical elements, including mirrors, lenses and beam combiners to receive the emission from the respective subsystem to the patient's eye and, in some cases, to redirect the emission from a patient's eye along the common propagation path to an appropriate director.

Controller 60 controls the operation of optical measurement system 1 and can receive input from any of optical coherence tomographer (OCT) subsystem 10, wavefront aberrometer subsystem 20, corneal topographer subsystem 30 for measuring one or more characteristics of a subject's eye, camera 40, fixation target 50, display 70 and operator interface 80 via communication paths 58. Controller 60 can include any suitable components, such as one or more processor, one or more field-programmable gate array (FPGA), and one or more memory storage devices. In many embodiments, controller 60 controls display 70 to provide for user control over the laser eye surgery procedure for pre-cataract procedure planning according to user specified treatment parameters as well as to provide user control over the laser eye surgery procedure. Communication paths 58 can be implemented in any suitable configuration, including any suitable shared or dedicated communication paths between controller 60 and the respective system components.

Operator interface 80 can include any suitable user input device suitable to provide user input to controller 60. For example, user interface devices 80 can include devices such as joystick 8, a keyboard, or a touchscreen display.

Figure 8A:
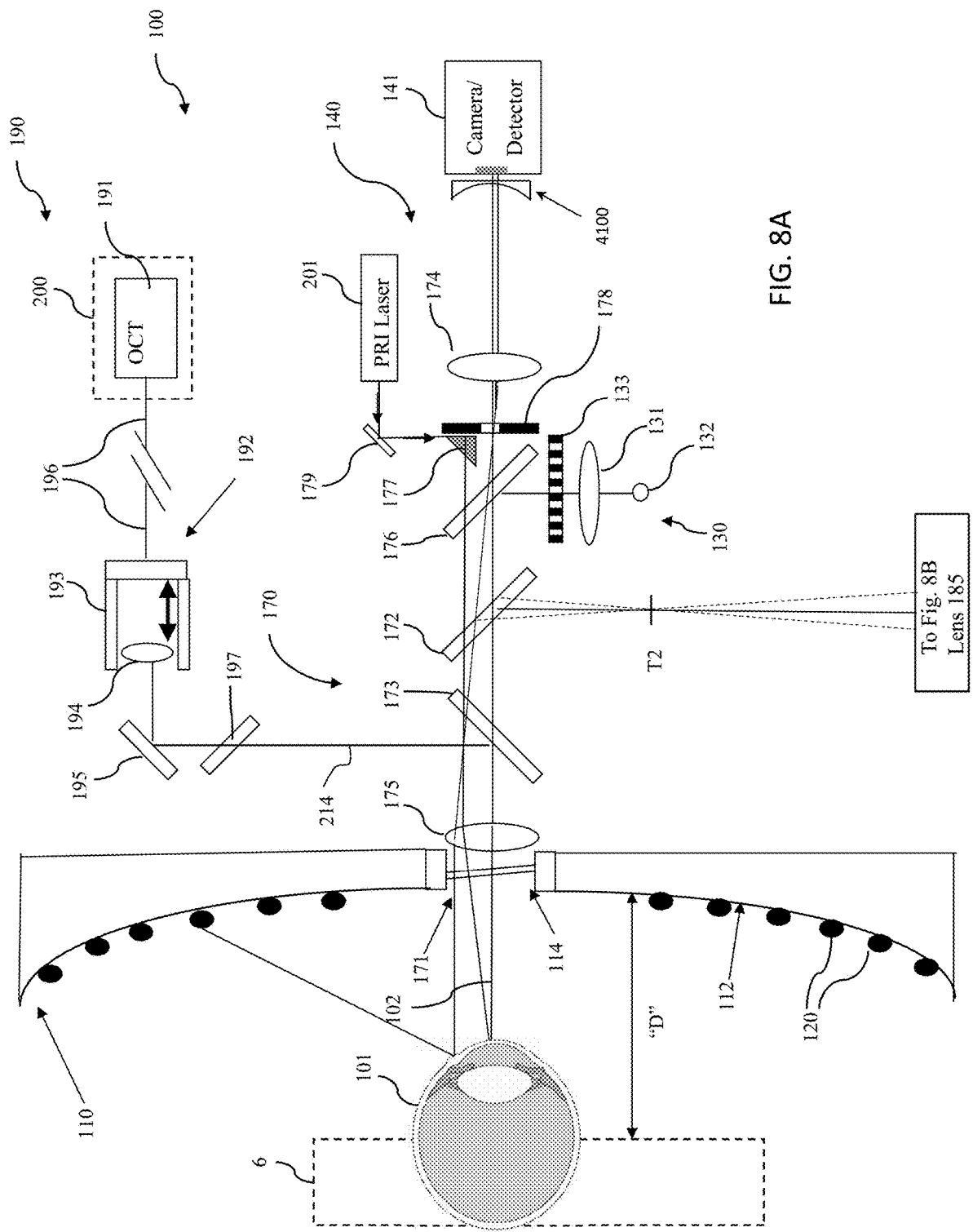
FIGS. 8A and 8B illustrate together an assembly illustrating a suitable configuration and integration of an optical coherence tomographer subsystem, a wavefront aberrometer subsystem, a corneal topographer subsystem, an iris imaging subsystem, a fixation target subsystem according to a non-limiting embodiment of the present invention.
Figure 8B:
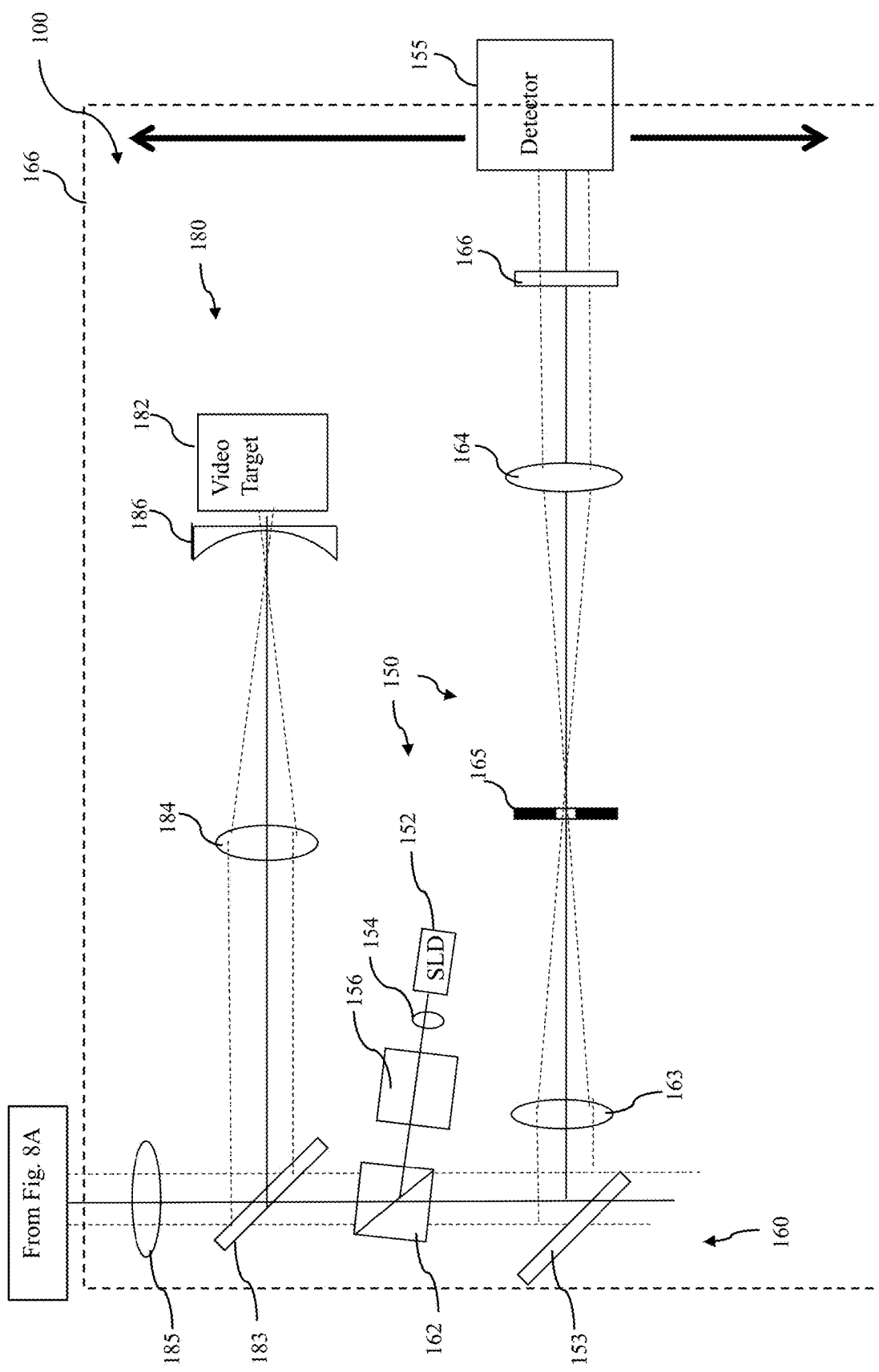

FIGS. 8A and 8B are simplified block diagrams illustrating an assembly 100 according to many embodiments which may be included in optical measurement system 1. Assembly 100 is a non-limiting example of suitable configurations and integration of an optical coherence tomography (OCT) subsystem 190, a wavefront aberrometer subsystem 150, a corneal topographer subsystem 140 for measuring one or more characteristics of a subject's eye 101, camera 40, a fixation target subsystem 180 and shared optics.

The shared optics generally comprise one or more components of a first optical system 170 disposed along a central axis 102 passing through the opening or aperture 114 of the structure 110. First optical system 170 directs light from the various light sources along the central axis 102 towards an eye 101 and establishes a shared or common optical path along which the light from the various light sources travel to eye 101. In one embodiment, optical system 170 comprises a quarter wave plate 171, a first beamsplitter 172, a second beamsplitter 173, an optical element (e.g., a lens) 174, a second lens 175, a third beamsplitter 176, and a structure including an aperture 178. Additional optical systems may be used in assembly 100 to direct light beams from one or more light sources to the first optical system 170. For example, a second optical system 160 directs light to the first optical system 170 from wavefront aberrometer subsystem 150 and comprises mirror 153, beam splitter 183 and lens 185.

Other configurations of assembly 100 may be possible and may be apparent to a person of skill in the art.

Corneal topographer subsystem 140 comprises a structure 110 having a principal surface 112 with an opening or aperture 114 therein; a plurality of first (or peripheral) light sources 120 provided on the principal surface 112 of structure 110; a Helmholz light source 130; and a detector, photodetector, or detector array 141, for example a camera.

In one embodiment, structure 110 has the shape of an elongated oval or "zeppelin" with openings or apertures at either end thereof. An example of such a structure is disclosed in Yobani Meji'a-Barbosa et al., "Object surface for applying a modified Hartmann test to measure corneal topography," APPLIED OPTICS, Vol. 40, No. 31 (Nov. 1, 2001) ("Meji'a-Barbosa"). In some embodiments, principal surface 112 of structure 110 is concave when viewed from the cornea of eye 101, as illustrated in FIG. 8A.

In one embodiment where principal surface 112 is concave, principal surface 112 has the shape of a conical frustum. Alternatively, principal surface 112 may have a shape of hemisphere or some other portion of a sphere, with an opening or aperture therein. Also, alternatively, principal surface 112 may have the shape of a modified sphere or conical frustum, with a side portion removed. Beneficially, such an arrangement may improve the ergonomics of assembly 100 by more easily allowing structure 110 to be more closely located to a subject's eye 1001 without being obstructed by the subject's nose. Of course, a variety of other configurations and shapes for principal surface 112 are possible.

In the embodiment of FIG. 8A, the plurality of first light sources 120 are provided on the principal surface 112 of structure 110 to illuminate the cornea of eye 101. In one embodiment, light sources 122 may comprise individual light generating elements or lamps, such as light emitting diodes (LEDs) and/or the tips of the individual optical fibers of a fiber bundle. Alternatively, principal surface 112 of structure 110 may have a plurality of holes or apertures therein, and one or more backlight lamps, which may include reflectors and/or diffusers, may be provided for passing lighting through the holes to form the plurality of first light sources 120 which project light onto the cornea of eye 101. Other arrangements are possible.

In another embodiment, structure 110 is omitted from assembly 100, and the first light sources 120 may be independently suspended (e.g., as separate optical fibers) to form a group of first light sources 120 arranged around a central axis, the group being separated from the axis by a radial distance defining an aperture in the group (corresponding generally to the aperture 114 in the structure 110 illustrated in FIG. 8A).

In operation, a ray (solid line) from one of the first light sources 120 is reflected by the cornea and passes through optical system 170, including field flattener (e.g., negative lens) 4100 to appear as a light spot on detector array 141. It will be appreciated that this ray is representative of a small bundle of rays that make it through optical system 170 and onto detector array 141, all of which will focus to substantially the same location on detector array 141. Other rays from that first light source 120 are either blocked by the aperture 178 or are otherwise scattered to not pass through the optical system 170. In similar fashion, light from the other first light sources 120 are imaged onto detector array 141 such that each one of first light sources 120 is imaged or mapped to a location on detector array 141 that may be correlated to a reflection location on the cornea of eye 101 and/or the shape of the cornea. Thus, detector array 141 detects the light spots projected thereon and provides corresponding output signals to a processor of controller 60 (FIG. 7). The processor determines the locations and/or shape of the light spots on detector array 141, and compares these locations and/or shapes to those expected for a standard or model cornea, thereby allowing the processor of controller 60 to determine the corneal topography. Alternatively, other ways of processing the spot images on detector array 141 may be used to determine the corneal topography of eye 101, or other information related to the characterization of eye 101.

Detector array 141 comprises a plurality of light detecting elements arranged in a two-dimensional array. In one embodiment, detector array 141 comprises such a charge-coupled device (CCD), such as may be found in a video camera. However, other arrangements such as a CMOS array, or another electronic photosensitive device, may be employed instead. Beneficially, the video output signal(s) of detector array 141 are provided to processor 60 which processes these output signals as described in greater detail below.

Assembly 100 also comprises a Helmholtz light source 130 configured according to the Helmholtz principle. As used herein, the term "Helmholtz source" or "Helmholtz light source" means one or a plurality of individual light sources disposed such that light from each of the individual light sources passes through an optical element having optical power, reflects off of a reference or test object, passes through the optical element, and is received by a detector, wherein light from the Helmholtz source is used to determine geometric and/or optical information of at least a portion of a surface of the reference or test object. In general, it is a characteristic of Helmholtz sources that the signal at the detector is independent of the relative position of the test or reference object relative to the Helmholtz source. As used herein, the term "optical element" means an element that refracts, reflects, and/or diffracts light and has either positive or negative optical power.

In such embodiments, the Helmholtz light source 130 is located at optical infinity with respect to eye 101. The Helmholtz principle includes the use of such infinite sources in combination with a telecentric detector system: i.e., a system that places the detector array at optical infinity with respect to the surface under measurement, in addition to insuring that the principal measured ray leaving the surface is parallel to the optical axis of the instrument. The Helmholtz corneal measurement principle has the Helmholtz light source at optical infinity and the telecentric observing system so that detector array 141 is also optically at an infinite distance from the images of the sources formed by the cornea. Such a measurement system is insensitive to axial misalignment of the corneal surface with respect to the instrument.

In one embodiment, the Helmholtz light source 130 comprises a second light source 132 which may comprise a plurality of lamps, such as LEDs or optical fiber tips. In one embodiment, second light source 132 comprises an LED and a plate 133 with plurality of holes or apertures in a surface that are illuminated by one or more backlight lamps with an optical element 131, which may comprise diffusers.

In one embodiment, lamps of second light sources 132 are located off the central optical axis 102 of assembly 100, and light from second light sources 132 is directed toward optical element 171 by third beamsplitter 176.

The operation of the topographer portion of system 100 may be conducted with the combined use of first light source 120 and the Helmholz light source 130. In operation, detector array 141 detects the light spots projected thereon from both Helmholz light source 130 (detected at a central portion of detector array 141) and first light sources 120 (detected at a peripheral portion of detector array 141) and provides corresponding output signals to processor. In general, the images of first light sources 120 that appear on detector array 141 emanate from an outer region of the surface of the cornea, and the images of Helmholz light source 130 that appear on detector array 141 emanate from a central or paraxial region of the surface of the cornea. Accordingly, even though information about the central region of the corneal surface (e.g., surface curvature) cannot be determined from the images of first light sources 120 on detector array 141, such information can be determined from the images of Helmholz light source 130 on detector array 141. A processor of controller 60 determines the locations and/or shapes of the light spots on detector array 141, and compares these locations and/or shapes to those expected based for a standard or model cornea, thereby allowing the processor to determine the corneal topography of eye 101. Accordingly, the topography of the entire corneal surface can be characterized by system 100 without a "hole" or missing data from the central corneal region.

Also, as explained above, while obtaining the corneal topography data for eye 101, an image of sclera 408 of eye 101 may be captured by detector array 141. The image may be processed by a processor (e.g., processor 61 of controller 60) executing a pattern recognition algorithm as known in the art to identify unique features of sclera 408, for example blood vessels 400. Processor 61 may execute a pattern recognition algorithm as a set of computer instructions stored in a memory (e.g., memory 62) associated with processor 61. Processor 61 may use the identified features from the image of eye 101 as fiducials or registration markers for the corneal topography data for eye 101. In some embodiments, processor 61 may store in memory 62 the corneal topographer data, the image of eye 61, and registration data which registers the corneal topography data to the locations of the identified features of fiducials in the image of eye 101. This set of data may be used by a surgical instrument in a subsequent surgery. For example, the surgical instrument may include a camera which is able to capture an image of eye 101, including the fiducials. By mapping the fiducials identified by system 100 to the same fiducials observed by the camera of the surgical instrument, the corneal topography data may be registered to the locations of the fiducials observed by the camera of the surgical instrument via the registration data of system 100.

A fourth light source 201 off the central axis 102 may be directed along optical axis 102 by mirrors 177, 179 disposed on or near the aperture 178, perpendicular to the optical axis 102 are configured as a pupil retroreflection illuminator. The pupil retroreflecton illuminator is configured to direct a disc of light toward patient's eye 101, whereby the disc of light may be reflected from reflective surfaces within eye 101, and the reflected light is transmitted by optical path 170 to detector 141. The pupil retroreflection illuminators may optionally be configured such that, when the patient's pupil is dilated, the disc of light from light source 201 is reflected from an implanted IOL to image the IOL, including any fiducial marks; if IOL is imperfectly placed, detector 141 may be used to determine IOL edges are decentered. Also, images from detector 141 using the pupil retroreflection illuminator may see folds, for instance, unfolded edge if the IOL did not unfold properly.

Wavefront aberrometer subsystem 150 of assembly 100 comprises a third light source 152 providing a probe beam and a wavefront sensor 155. Wavefront aberrometer subsystem 150 preferably further comprises a collimating lens 154, a polarizing beamsplitter 156, an adjustable telescope comprising a first optical element, lens 163 and a second optical element, lens 164, a movable stage or platform 166, and a dynamic-range limiting aperture 165 for limiting a dynamic range of light provided to wavefront sensor 155 to preclude data ambiguity. Light from the wavefront aberrometer subsystem is directed to one of the constituent optical elements of the optical system 170 disposed along a central axis 102 passing through the opening or aperture 114 of the structure 110. It will be appreciated by those of skill in the art that the lenses 163, 164, or any of the other lenses discussed herein, may be replaced or supplemented by another type of converging or diverging optical element, such as a diffractive optical element.

Light source 152 may be an 840 nm SLD (super luminescent laser diode). An SLD is like a laser in that the light originates from a very small emitter area. However, unlike a laser, the spectral width of the SLD is very broad, about 40 nm. This tends to reduce speckle effects and improve the images that are used for wavefront measurements.

Beneficially, wavefront sensor 155 may be a Shack-Hartmann wavefront sensor comprising a detector array and a plurality of lenslets for focusing received light onto its detector array. In that case, the detector array may be a CCD, a CMOS array, or another electronic photosensitive device. However, other wavefront sensors may be employed instead. Embodiments of wavefront sensors which may be employed in one or more systems described herein are described in U.S. Pat. No. 6,550,917, issued to Neal et al. on Apr. 22, 2003, and U.S. Pat. No. 5,777,719, issued to Williams et al. on Jul. 7, 1998, both of which patents are hereby incorporated herein by reference in their entirety.

The aperture or opening in the middle of the group of first light sources 120 (e.g., aperture 114 in principal surface 112 of structure 110) allows assembly 100 to provide a probe beam into eye 101 to characterize its total ocular aberrations. Accordingly, third light source 152 supplies a probe beam through a light source polarizing beam splitter 156 and polarizing beam splitter 162 to first beamsplitter 172 of optical system 170. First beamsplitter 172 directs the probe beam through aperture 114 to eye 101. Preferably, light from the probe beam is scattered from the retina of eye 100, and at least a portion of the scattered light passes back through aperture 114 to first beamsplitter 172. First beamsplitter 172 directs the back scattered light back through beam splitter 172 to polarizing beamsplitter 162, mirror 153 to wavefront sensor 155.

Wavefront sensor 155 outputs signals to a processor of controller 60 which uses the signals to determine ocular aberrations of eye 101. Preferably, the processor can better characterize eye 101 by considering the corneal topography of eye 101 measured by corneal topography subsystem 140, which may also be determined by the processor based on outputs of detector array 141, as explained above.

In operation of wavefront aberrometer subsystem 150, light from light source 152 is collimated by lens 154. The light passes through light source polarizing beam splitter 156. The light entering light source polarizing beam splitter 156 is partially polarized. Light source polarizing beam splitter 156 reflects light having a first, S, polarization, and transmits light having a second, P, polarization so the exiting light is 100% linearly polarized. In this case, S and P refer to polarization directions relative to the hypotenuse in light source polarizing beam splitter 156.

Light from light source polarizing beam splitter 156 enters polarizing beamsplitter 162. The hypotenuse of polarizing beamsplitter 162 is rotated 90 degrees relative to the hypotenuse of light source polarizing beamsplitter 156 so the light is now S polarized relative the hypotenuse of polarizing beamsplitter 162 and therefore the light reflects upwards. The light from polarizing beamsplitter 162 travels upward and passes through toward beam splitter 172, retaining its S polarization, and then travels through quarter wave plate 171. Quarter wave plate 171 converts the light to circular polarization. The light then travels through aperture 114 in principal surface 112 of structure 110 to eye 101. Preferably, the beam diameter on the cornea is between 1 and 2 mm. Then the light travels through the cornea and focuses onto the retina of eye 101.

The focused spot of light becomes a light source that is used to characterize eye 101 with wavefront sensor 155. Light from the probe beam that impinges on the retina of eye 101 scatters in various directions. Some of the light reflects back as a semi-collimated beam back towards assembly 100. Upon scattering, about 90% of the light retains its polarization. So, the light traveling back towards assembly is substantially still circularly polarized. The light then travels through aperture 114 in principal surface 112 of structure 110, through quarterwave plate 171, and is converted back to linear polarization. Quarterwave plate 171 converts the polarization of the light from the eye's retina so that it is P polarized, in contrast to probe beam received from third light source 150 having the S polarization. This P polarized light then reflects off of first beamsplitter 172, and then reaches polarizing beamsplitter 162. Since the light is now P polarized relative the hypotenuse of polarizing beamsplitter 162, the beam is transmitted and then continues onto mirror 153. After being reflected by mirror 153, light is sent to an adjustable telescope comprising a first optical element 164 and a second optical element (e.g., lens) 163 and a movable stage or platform 166. The beam is also directed through a dynamic-range limiting aperture 165 for limiting a dynamic range of light provided to wavefront sensor 155 to preclude data ambiguity.

When wavefront sensor 155 is a Shack-Hartmann sensor, the light is collected by the lenslet array in wavefront sensor 155 and an image of spots appears on the detector array (e.g., CCD) in wavefront sensor 155. This image is then provided to a processor of controller 60 and analyzed to compute the refraction and aberrations of eye 101.

OCT subsystem 190 of assembly 100 may comprise an OCT assembly 191, and a third optical path 192 which directs the OCT beam of the OCT light source to the first optical path 170. The third optical path 192 may comprise a fiber optic line 196, for conducting the OCT beam from the OCT light source of OCT assembly 191, a Z-scan device 193 operable to alter the focus of the beam in the Z-direction (i.e., along the direction of propagation of the OCT beam) under control of the controller, and X-scan device 195, and a Y-scan device 197 operable to translate the OCT beam in the X and Y directions (i.e., perpendicular to the direction of propagation of the of the OCT beam), respectively, under control of controller 60. The OCT light source and reference arm may be incorporated into assembly 100 of optical measurement system 1 shown in FIG. 8A. Alternatively, OCT assembly 191 may be housed in a second unit or housing 200 and the OCT beam from the OCT source may be directed from second unit 200 to the main unit by optical pathway 192.

Beneficially, the OCT systems and methods employed in optical measurement system 1 and assembly 100 may employ swept source optical coherence tomography (SS-OCT) as described above. Beneficially, optical measurement system 1, assembly 100 and OCT subsystem 190 may each comprise OCT interferometer 1000, 3000 or 4000.

As explained above, in SS-OCT, a rapid-scanning laser source is employed. By rapidly sweeping the source wavelength over a broad wavelength range, and collecting all the scattering and reflection information at each wavelength and at each position, the collected spectral data may be inverse-Fourier-transformed to recover the spatial depth-dependent information for the object under test (e.g., eye 101).

In operation, as shown in FIG. 8A, after exiting connector 212, an OCT probe beam 214 may be collimated, for example using a collimating optical fiber 196. Following collimating fiber 196 OCT probe beam 214 is directed to Z-scan device 193 operable to change the focal point of OCT probe beam 214 in the Z-direction, and X- and Y-scan devices 195 and 197, which are operable to scan the OCT beam in X and Y-directions perpendicular to the Z-direction.

Following the collimating optical fiber 196, OCT probe beam 214 continues through a Z-scan device 193. Z-scan device 193 may comprise a Z-telescope 194 which is operable to scan focus position of OCT probe beam 214 in the patient's eye 101 along the Z axis. For example, Z-telescope 194 may include a Galilean telescope with two lens groups (each lens group includes one or more lenses). One of the lens groups moves along the Z axis about the collimation position of Z-scan device 193. In this way, the focus position in the patient's eye 101 moves along the Z axis. In general, there is a relationship between the motion of lens group and the motion of the focus point. The exact relationship between the motion of the lens and the motion of the focus in the Z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. Z-telescope 194 functions as a Z-scan device for changing the focus point of OCT probe beam 214 in patient's eye 101. Z-scan telescope 194 can be controlled automatically and dynamically by controller 60 and selected to be independent or to interplay with X and Y scan devices 195 and 197.

After passing through the z-scan device, the OCT probe beam 214 is incident upon an X-scan device 195, which is operable to scan the OCT probe beam 214 in the X direction, which is dominantly transverse to the Z axis and transverse to the direction of propagation of OCT probe beam 214. X-scan device 195 is controlled by controller 60, and can include suitable components, such as a lens coupled to a MEMS device, a motor, galvanometer, or any other well-known optic moving device. The relationship of the motion of OCT probe beam 214 as a function of the motion of the actuator of X-scan device 195 does not have to be fixed or linear. Modeling or calibrated measurement of the relationship or a combination of both can be determined and used to direct the location of OCT probe beam 214.

After being directed by the X-scan device 195, OCT probe beam 214 is incident upon a Y scan device 197, which is operable to scan OCT probe beam 214 in the Y direction, which is dominantly transverse to the X and Z axes. Y-scan device 197 is controlled by the controller 60, and can include suitable components, such as a lens coupled to a MEMS device, motor, galvanometer, or any other well-known optic moving device. The relationship of the motion of the beam as a function of the motion of the Y actuator of Y-scan device 197 does not have to be fixed or linear. Modeling or calibrated measurement of the relationship or a combination of both can be determined and used to direct the location of OCT probe beam 214. Alternatively, the functionality of X-Scan device 195 and Y-Scan device 197 can be provided by an XY-scan device configured to scan OCT probe beam 214 in two dimensions transverse to the Z axis and the propagation direction of OCT probe beam 214. The X-scan and Y scan devices 195, 197 change the resulting direction of OCT probe beam 214, causing lateral displacements of OCT probe beam 214 located in the patient's eye 101.

OCT probe beam 214 is then directed to beam splitter 173 through lens 175 through quarter wave plate 171 and aperture 114 and to the patient eye 101. Reflections and scattering off from structures within the eye provide return beams that retrace back through the patient interface quarter wave plate 171, lens 175, beam splitter 173, Y-scan device 197, X-scan device 195, Z-scan device 193, optical fiber 196 and beam combiner 204 (FIG. 6), and back into the OCT detection device 220. The returning back reflections of the sample arm 201 are combined with the returning reference portion 206 and directed into the detector portion of the OCT detection device 220, which generates OCT signals in response to the combined returning beams. The generated OCT signals that are in turn interpreted by controller 60 to determine the spatial disposition of the structures of interest in patient's eye 101. The generated OCT signals can also be interpreted by the controller to determine the spatial disposition of the structures of interest in the patient's eye 101. The generated OCT signals can also be interpreted by the control electronics to align the position and orientation of the patient eye within the patient interface.

Optical measurement systems disclosed herein may comprise an iris imaging subsystem 40. Iris imaging subsystem 40 generally may comprise an infrared light source, for example an infrared light source 152, and detector 141. In operation light from light source 152 is directed along second optical path 160 to first optical path 170 and is subsequently directed to eye 101 as described above. Light reflected from the iris of eye 101 is reflected back along first optical path 170 to detector 141. In normal use, an operator will adjust a position or alignment of system 100 in X, Y and Z directions to align the patient according to the image detector array 141. In one embodiment of the iris imaging subsystem, eye 101 is illuminated with infrared light from light source 152. In this way, the wavefront obtained by wavefront sensor 155 will be registered to the image from detector array 141.

The image that the operator sees is the iris of eye 100. The cornea generally magnifies and slightly displaces the image from the physical location of the iris. So, the alignment that is done is to the entrance pupil of the eye. This is generally the desired condition for wavefront sensing and iris registration.

Iris images obtained by the iris imaging subsystem may be used for registering and/or fusing the multiple data sets obtained by the various subsystems of optical measurement system 1 by methods described, for instance, in "Method for registering multiple data sets," U.S. patent application Ser. No. 12/418,841, which is incorporated herein by reference. As set forth in application Ser. No. 12/418,841, wavefront aberrometry may be fused with corneal topography, optical coherence tomography and wavefront, optical coherence tomography and topography, pachymetry and wavefront, etc. For instance, with image recognition techniques it is possible to find the position and extent of various features in an image. Regarding iris registration images, features that are available include the position, size and shape of the pupil, the position, size and shape of the outer iris boundary (OIB), salient iris features (landmarks) and other features as are determined to be needed. Using these techniques, both patient movement between measurements (and/or during a measurement sequence) can be identified, as well as changes in the eye itself (including those induced by the measurement, such as changes in the size of the pupil, changes in pupil location, etc.).

In many embodiments, optical measurement system 1 includes a target fixation subsystem 50 (FIG. 7), and assembly 100 shown in FIGS. 8A and 8B includes fixation target subsystem 180 which includes a fixation target 182 for the patient to view. Fixation target subsystem 180 is used to control the patient's accommodation and alignment, because it is often desired to measure the refraction and wavefront aberrations when eye 100 is focused at its far point (e.g., because LASIK treatments are primarily based on this). In the target fixation subsystem, a projection of a target, for instance, a cross-hair pattern is projected onto the eye of the patient, the cross-hair pattern being formed by a backlit LED and a film.

In operation, light originates from the light source 152 or, alternatively, from video target backlight 182 and lens 186. Lens 185 collects the light and forms an aerial image T2. This aerial image is the one that the patient views. The patient focus is maintained on aerial image 182 during measurement to maintain the eye in a fixed focal position.

The operating sequence the optical measurement system and methods of the present is not particularly limited. A scan of the patient's eye may comprise one or more of a wavefront aberrometry measurement of a patient's eye utilizing the wavefront aberrometry subsystem, a corneal topography measurement of a patient's eye and an OCT scan of the patient's eye using the OCT subsystem, wherein the OCT scan includes a scan at each or one or more locations within the eye of the patient. These locations of the OCT scan may correspond to the location of the cornea, the location of the anterior portion of the lens, the location of the posterior portion of the lens and the location of the retina. In a preferred embodiment, the operating sequence includes each of a wavefront aberrometry measurement, a corneal topography measurement and an OCT scan, wherein the OCT scan measures at least the locations of the retina, the cornea and one of anterior portion of the patient's lens. An iris image may be taken simultaneously with or sequentially with each of the measurements taken with wavefront aberrometry subsystem, the corneal topography subsystem and the OCT subsystem, including an iris image take simultaneously with or sequentially with the location of each OCT scan. This results in improved accuracy in the 3-dimensional modeling of the patient's eye by permitting the various data sets to be fused and merged into a 3-dimensional model.

Optical measurement system 1 and the optical measurements obtained therewith may be used pre-operatively, i.e. before a cataract surgery or other surgical procedure, for, e.g., eye biometry and other measurements, diagnostics and surgical planning. Surgical planning may include one or more predictive models. In the one or more predictive models, one or more characteristics of the postoperative condition of the patient's eye or vision is modeled based on one or more selected from the group consisting of pre-operative measurements obtained from the optical measurement system 1, a contemplated surgical intervention, and on or more algorithms or models stored in the memory of the optical measurement system 1 and executed by the processor. The contemplated surgical intervention may include the selection of an IOL for placement, the alignment of a toric IOL in the eye, the selection of an IOL characteristic, the nature or type of incision to be used during surgery (e.g., relaxation incision), or one or more post-operative vision characteristics requested by the patient.

Optical measurement system 1 and the optical measurements obtained therewith may be used intra-operatively, i.e., during a cataract surgery or other surgical procedure, for, e.g., intraoperative eye diagnostics, determining IOL placement and position, surgical planning, and control/or of a laser surgical system. For instance, in the case of laser cataract surgical procedure, any measurement data obtained preoperatively by the optical measurement instrument may be transferred to a memory associated with a cataract laser surgical system for use before, during or after either the placement of a capsulotomy, fragmentation or a patient's lens or IOL placement during the cataract surgery. In some embodiments, measurements using optical measurement system 1 may be taken during the surgical procedure to determine whether the IOL is properly placed in the patient's eye. In this regard, conditions measured during the surgical procedure may be compared to a predicted condition of the patient's eye based on pre-operative measurements, and a difference between the predicted condition and the actual measured condition may be used to undertake additional or corrective actions during the cataract surgery or other surgical procedure.

Optical measurement system 1 and the optical measurements obtained therewith may be used postoperatively, i.e., after a cataract surgery or other surgical procedure, for, e.g., post-operative measurement, postoperative eye diagnostics, postoperative IOL placement and position determinations, and corrective treatment planning if necessary. The postoperative testing may occur sufficiently after the surgery that the patient's eye has had sufficient time to heal and the patient's vision has achieved a stable, postsurgical state. A postoperative condition may be compared to one or more predicted condition performed pre-operatively, and a difference between the preoperatively predicted condition and the postoperatively measured condition may be used to plan additional or corrective actions during the cataract surgery or other surgical procedure.

Optical measurement system 1, including the corneal topography subsystem, the OCT subsystem and the wavefront aberrometry subsystem, utilizing a suitable operating sequence as disclosed herein, is operable to measure one, more than one or all of the following: ocular biometry information, anterior corneal surface information, posterior corneal surface information, anterior lens surface information, posterior lens surface information, lens tilt information and lens position information. In some embodiments, the ocular biometry information may include a plurality of central corneal thicknesses (CCT), an anterior chamber depth (ACT), a pupil diameter (PD), a white to white distance (WTW), a lens thickness (LT), an axial length (AL) and a retinal layer thickness. This measurement data may be stored in memory 62 associated with controller 60. The plurality of characteristics may be measured preoperatively, and where appropriate, intra-operatively, and postoperatively.

In some embodiments, memory 62 associated with controller 60 may store intraocular lens (IOL) model data for a plurality of IOL models, each of the IOL models having associated with it a plurality of predetermined parameters selected from the group consisting of dioptic power, refractive index, asphericity, toricity, haptic angulation and lens filter. The IOL data may be used by one or more processors of optical measurement system 1, in conjunction with measurement data of a subject's eye obtained by optical measurement system 1, for cataract diagnostics or cataract treatment planning, which may include specifying and/or selecting a particular IOL for a subject's eye. For example, one or more processors of optical measurement system 1 may execute an algorithm which includes: accessing the plurality of IOL models stored in, and for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL for the subject's eye from the plurality of IOL models corresponding to the optimized IOL based on a predetermined criteria.

In some embodiments, one or more processors of optical measurement system 1 may execute an algorithm comprising: determining a desired postoperative condition of the subject's eye; empirically calculating a post-operative condition of the eye based at least partially on the measured eye characteristics; and predictively estimating, in accordance with an output of said empirically calculating and the eye characteristics, at least one parameter of an intraocular lens for implantation into the subject's eye to obtain the desired postoperative condition.

In many embodiments, the eye imaging and diagnostic system further comprises a memory operable to store Intraocular Lens ("IOL") Data, the IOL data including a plurality of dioptic power, anterior and posterior radius, IOL thickness, refractive index, asphericity, toricity, echelette features, haptic angulation and lens filter.

In many embodiments, the eye imaging and diagnostic system further comprises a memory operable to store intraocular lens ("IOL") model data for a plurality of IOL models, IOL model having associated with a plurality of predetermined parameters selected from the group consisting of dioptic power, anterior and posterior radius, IOL thickness, refractive index, asphericity, toricity, echelette features, haptic angulation and lens filter.

An improved system for selecting an intraocular lens (IOL) for implantation, may comprise: a memory operable to store data acquired from each of the corneal topography subsystem, the wavefront sensor subsystem and the Optical Coherence Tomography subsystem, wherein the stored data includes a plurality of ocular biometry information, anterior corneal surface information, posterior corneal surface information, anterior lens surface information, and posterior lens surface information, lens tilt information and lens position information; the memory further operable to store intraocular lens ("IOL") model data for a plurality of IOL models, IOL model having associated with it a plurality of predetermined parameters selected from the group consisting of dioptic power, anterior and posterior radius, IOL thickness, refractive index, asphericity, toricity, echelette features, haptic angulation and lens filter; and a processor coupled to the memory, the processor deriving the treatment of the eye of the patient applying, for each of the plurality of identified IOL Model, to: (1) predict a position of one of the identified IOL Models when implanted in the subject eye, based on the plurality of characteristics; (2) simulate the subject eye based on the plurality of IOL predetermined parameters and the predicted IOL position; (3) perform one or more of ray tracing and a IOL spherical equivalent (SE) and cylinder (C) power calculation, as well as optionally, to determine the optimum IOL orientation based on said eye model; and (4) propose one IOL power for one or more IOL models from the plurality of IOLs corresponding to the optimized IOL(s) based on predetermined criteria; and (5) show the simulated optical quality and/or visual performance provided by each of the proposed IOL models for distance and/or for any other vergence.

A method of selecting an intraocular lens (IOL) to be implanted in a subject's eye, may comprise: measuring a plurality of eye characteristics comprising ocular biometry information, anterior corneal surface information, posterior corneal surface information, anterior lens surface information, and posterior lens surface information, lens tilt information and lens position information; and for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation and lens filter: (1) modeling the subject eye with the intraocular lens; (2) simulating the subject eye based on the plurality of IOL predetermined parameters and the predicted IOL position; (3) performing a ray tracing and a IOL spherical equivalent (SE) and cylinder (C) power calculation, as well as determine the optimum IOL orientation based on said eye model; and (4) proposing one IOL power for one or more IOL models from the plurality of IOLs corresponding to the optimized IOL(s) based on predetermined criteria; and optionally (5) show the simulated optical quality and/or visual performance provided by each of the proposed IOL models for distance and/or for any other vergence.

A tangible computer-readable storage device may store computer instructions which, when read by a computer, cause the computer to perform a method comprising: receiving a plurality of eye characteristics comprising ocular biometry information, anterior corneal surface information, posterior corneal surface information, anterior lens surface information, and posterior lens surface information, lens tilt information and lens position information; for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation and lens filter: (1) simulating a geometry of the subject eye with each of the plurality of intraocular lenses (IOL) implanted, in accordance with the plurality of eye characteristics; (2) performing a ray tracing and a IOL spherical equivalent (SE) and cylinder (C) power calculation, as well as optionally determining the optimum IOL orientation based on said eye model; (3) proposing one IOL power for one or more IOL models from the plurality of IOLs corresponding to the optimized IOL(s) based on predetermined criteria; and optionally (4) showing the simulated optical quality and/or visual performance provided by each of the proposed IOL models for distance and/or for any other vergence.

A method of predicting the intraocular lens position may comprise: determining a plurality of eye characteristics before cataract surgery, comprising ocular biometry information, anterior corneal surface information, posterior corneal surface information, anterior lens surface information, and posterior lens surface information, lens tilt information and lens position information; determining a plurality of eye characteristics after cataract surgery, comprising ocular biometry information, anterior corneal surface information, posterior corneal surface information, anterior lens surface information, and posterior lens surface information, lens tilt information and lens position information; calculating or measuring, based on a mathematical relationship, a distance from the apex to a plane of the intraocular lens after an ocular surgical procedure; calculating an optical power of the intraocular lens suitable for providing a predetermined refractive outcome; wherein a mathematical relationship is found between the preoperative and postoperative eye characteristics that accurately predict the measured distance from the apex to the plane where the intraocular lens is.

An improved system for planning a refractive treatment of an eye of a patient, may comprise: a memory operable to store eye measurement data comprising ocular biometry information, anterior corneal surface information, posterior corneal surface information, anterior lens surface information, and posterior lens surface information, lens tilt information and lens position information; a processor coupled to the memory, the processor deriving the treatment of the eye of the patient applying an effective treatment transfer function, wherein the effective treatment transfer function is derived from, for each of a plurality of prior eye treatments, a correlation between a pre-treatment vector characterizing the eye measurement data before treatment, and a post-treatment vector characterizing post-treatment eye measurement data of the associated eye; an output coupled to the processor so as to transmit the treatment to facilitate improving refraction of the eye of the patient. The processor may comprise tangible media embodying machine readable instructions for implementing the derivation of the treatment.

An improved method for planning a refractive treatment of an eye of a patient may comprise: measuring a plurality of ocular biometry information, anterior corneal surface information, posterior corneal surface information, anterior lens surface information, and posterior lens surface information, lens tilt information and lens position information.

A method of customizing at least one parameter of an intraocular lens, may comprise: measuring a plurality of eye characteristics comprising ocular biometry information, anterior corneal surface information, posterior corneal surface information, anterior lens surface information, and posterior lens surface information, lens tilt information and lens position information; determining a desired postoperative condition of the eye; empirically calculating a postoperative condition of the eye based at least partially on the measured eye characteristics; and predictively estimating, in accordance with an output of said empirically calculating and the eye characteristics, with at least one parameter of the intraocular lens to obtain the desired postoperative condition.

A method of adjusting the refractive power in an eye of a patient who has undergone cataract surgery may comprise: measuring a plurality of post-operative eye characteristics in an eye of a patient who has previously undergone cataract surgery, the eye characteristics comprising ocular biometry information, anterior corneal surface information, posterior corneal surface information, anterior lens surface information, and posterior lens surface information, lens tilt information and lens position information; identifying a plurality of corrective procedure based at least partially on one of (1) a comparison of at least one measured pre-operative eye characteristic and the corresponding measured post-operative eye characteristic; and (2) a comparison of at least one predicted post-operative eye characteristic and the corresponding measured post-operative eye characteristic; for each of a plurality of corrective procedures: modeling the subject eye with the corrective procedure; modeling the subject eye based on the corrective procedure; performing one of a ray tracing and a power calculation based on said eye model; and selecting a corrective procedure from the plurality of IOL models corresponding to the optimized IOL based on a predetermined criteria.

In some embodiments, the system further comprises a processor configured to execute an algorithm. The algorithm comprises, for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL from the plurality of IOL models corresponding to the optimized IOL based on a predetermined criteria.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

All patents and patent applications cited here are hereby incorporated by reference hereby reference in their entirety.

The use of the terms "a" and "an" and "the" and similar referents in the context of describing the invention (especially in the context of the following claims) are to be construed to cover both the singular and the plural, unless otherwise indicated here or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values here are merely intended to serve as a shorthand method of referring individually to each separate value falling within the range, unless otherwise indicated herein, and each separate value is incorporated into the specification as if it were individually recited herein. All methods described here can be performed in any suitable order unless otherwise indicated here or otherwise clearly contradicted by context. The use of any and all examples, or exemplary language (e.g., "such as") provided herein, is intended merely to better illuminate embodiments of the invention, and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made and remain within the concept without departing from the spirit or scope of the invention. Such variations would become clear to one of ordinary skill in the art after inspection of the specification, drawings and claims herein. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

We claim:

1. A system, comprising:
    a group of first light sources arranged around a central axis, the group being separated from the central axis by a radial distance defining an aperture in the group;
    a plurality of second light sources;
    a detector array; and
    an optical system adapted to direct light from the second light sources through the aperture to a cornea of an eye, and to direct light from virtual images of the first light sources and the second light sources from the cornea, through the aperture, to the detector array, wherein the optical system includes a pair of positive lenses and a field flattener which comprises a negative lens and is disposed between the pair of positive lenses and the detector array and in front of the detector array without additional lenses between the field flattener and the detector array, such that a shape of a surface that forms best focus on the detector array curves away from the detector array to be concave on a side opposite the detector array and matches a shape of a sclera of the eye, wherein the optical system including the field flattener forms an image of the sclera focused on the detector array,
    wherein the detector array is configured to detect the light from the virtual images of the first light sources and the second light sources from the cornea and in response thereto to output pixel data.

2. The system of claim 1, wherein, the system further comprises a processor configured to process the pixel data to produce corneal topography data for the eye.

3. The system of claim 1, wherein the processor is configured to detect features of the sclera from the image of the sclera.

4. The system of claim 3, wherein the features are blood vessels.

5. The system of claim 4, wherein the processor is configured to register the corneal topography data to locations of the blood vessels of the sclera.

6. The system of claim 1, further comprising a wavefront aberrometer, an optical coherence tomographer, an iris imaging system and a structure having the aperture therethrough, wherein all of the wavefront aberrometer, optical coherence tomographer, and the iris imaging system direct light to the eye through the aperture.

7. A method, comprising:
aligning a measurement instrument, including a corneal topographer, to an eye;
illuminating a sclera of the eye;
producing a pattern of light spots on a cornea of the eye;
directing light from a virtual image of the pattern of light spots from the cornea of the eye, through an optical system which includes a pair of positive lenses and a field flattener, to a sensor of a camera of the measurement instrument while the camera views the sclera of the eye, in focus, wherein the field flattener comprises a negative lens and is disposed between the pair of positive lenses and the camera and in front of the camera without additional lenses between the field flattener and the camera, and wherein the optical system including the field flattener forms a surface of best focus on the detector array which curves away from the detector array to be concave on a side opposite the detector array and which matches a shape of the sclera;
obtaining corneal topography data from the light from a virtual image of the pattern of light spots from the cornea which appears at the sensor;
the measurement instrument detecting sclera features from the image of the eye at the camera; and
registering the corneal topography data to locations of the detected sclera features.

8. The method of claim 7, wherein the field flattener causes a shape of a surface that forms best focus on the sensor to curve away from the sensor to be concave on a side opposite the sensor.

9. The method of claim 7, wherein producing the pattern of light spots on the cornea of the eye comprises:
providing a group of first light sources arranged around a central axis, the group being separated from the axis by a radial distance defining an aperture in the group;
providing a plurality of second light sources; and
directing light from the second light sources through the aperture to the cornea of an eye.

10. The method of claim 9, wherein the step of obtaining corneal topography data includes the sensor outputting pixel data, and processing the pixel data to produce the corneal topography data.

11. The method of claim 7, wherein the sclera features are sclera blood vessels.

12. The method of claim 7, wherein the measurement instrument includes a wavefront aberrometer, an optical coherence tomographer, an iris imaging system and a structure having the aperture therethrough, wherein all of the wavefront aberrometer, optical coherence tomographer, and the iris imaging system direct light to the eye through the aperture.

13. The method of claim 7, further comprising:
using a second camera of a surgical instrument to detect the scleral features which were previously detected from the image of the eye at the camera of the measurement instrument; and
the surgical instrument registering the corneal topography data to locations of the scleral features which were detected by the surgical instrument, using the registration of the corneal topography data to the locations of the scleral features which were detected by the measurement instrument.

14. A system, comprising:
a light pattern generator configured to produce a light pattern on a cornea of an eye;
one or more light sources for illuminating the sclera;
a detector array; and
an optical system adapted to direct light from a virtual image of the light pattern from the cornea of the eye to the detector array and to produce an image of a sclera of the eye, wherein the optical system includes a field flattener which is disposed in front of the detector array without additional lenses between the field flattener and the detector array, wherein the optical system including the field flattener forms a surface of best focus on the detector array which curves away from the detector array to be concave on a side opposite the detector array and which matches a shape of the sclera, wherein the optical system including the field flattener forms an image of the sclera focused on the detector array.

15. The system of claim 14, further comprising a processor configured to detect features of the sclera from the image of the sclera.

16. The system of claim 14, wherein the optical system comprises a pair of positive lenses, and wherein the field flattener comprises a negative lens disposed between the pair of positive lenses and the detector array.

17. The system of claim 14, wherein the optical system comprises a pair of positive lenses, and wherein the field flattener comprises a negative achromatic lens disposed between the pair of positive lenses and the detector array.

* * * * *